United States Patent [19]

Takase et al.

[11] 4,410,724
[45] Oct. 18, 1983

[54] PROCESS FOR PRODUCTION OF O-(2,6-DICHLOROANILINO)-PHENYLACETIC ACID

[75] Inventors: Muneaki Takase, Oizumi; Tadahiro Nakamura, Niiza; Kazuo Kamiya, Higashikurume; Toshiyuki Takezawa, Urawa; Hiroaki Yamazaki, Fujishiro; Takashi Iwaki, Tokyo, all of Japan

[73] Assignee: Zenyaku Kogyo Kabushiki Kaisha, Tokyo, Japan

[21] Appl. No.: 312,080

[22] Filed: Oct. 16, 1981

[30] Foreign Application Priority Data

Oct. 20, 1980 [JP] Japan ................................. 55-146500

[51] Int. Cl.$^3$ ............................................. C07C 99/00
[52] U.S. Cl. ................................................... 562/456
[58] Field of Search ................ 562/456, 457; 564/168, 564/163, 405, 431, 435

[56] References Cited

U.S. PATENT DOCUMENTS

| 2,476,170 | 7/1949 | Widiger | 564/405 |
| 2,924,620 | 2/1960 | Miller | 564/405 |
| 3,989,746 | 11/1976 | Nohara et al. | 562/457 |
| 4,189,595 | 2/1980 | Sakoda | 562/457 |
| 4,283,532 | 8/1981 | Nohara | 564/168 |

FOREIGN PATENT DOCUMENTS

| 52-71439 | of 0000 | Japan | 562/456 |
| 54-73749 | of 0000 | Japan | 562/456 |
| 55-374 | of 0000 | Japan | 562/456 |
| 55-72152 | of 0000 | Japan | 562/456 |

OTHER PUBLICATIONS

Bergmann, Bull. Chem. Soc. Fr., 1968, #3, pp. 1090–1091, (1968).

*Primary Examiner*—James H. Reamer
*Attorney, Agent, or Firm*—Scrivener, Clarke, Scrivener and Johnson

[57] ABSTRACT

There is provided a process for production of o-(2,6-dichloroanilino)phenylacetic acid or a salt thereof by reacting o-chlorophenylacetic acid or an alkali metal salt thereof with 2,6-dichloroaniline in the presence of a base and at least 0.5 mol of a copper catalyst per mol of o-chlorophenylacetic acid in a polar solvent.

12 Claims, No Drawings

PROCESS FOR PRODUCTION OF O-(2,6-DICHLOROANILINO)-PHENYLACETIC ACID

FIELD OF THE INVENTION

The present invention relates to a process for production of o-(2,6-dichloroanilino)phenylacetic acid of formula (I):

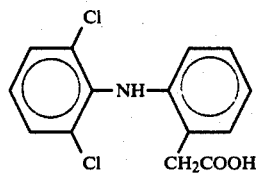

BACKGROUND OF THE INVENTION

A compound of above formula (I) is generally called "Diclofenac" and has anti-inflammatory, analgetic and anti-pyretic effects as disclosed in Japanese Pat. No. 23418/1967.

Processes for production of the compound (I) and salts thereof have been disclosed in Japanese Pat. Nos. 23418/1967, 27573/1969, 11295/1970 and 20469/1977. However, those known processes have drawbacks in that they comprise many steps and that yield of the intended product after completion of the all steps is poor. The processes are, therefore, industrially unsatisfactory.

Studies were already made for the purpose of simplifying the steps, resulting in obtaining the intended compound (I) by reacting o-bromo-, o-iodophenylacetic acid or a salt thereof with 2,6-dichloroaniline or an N-substituted derivative thereof in one step as disclosed in Japanese Patent Public Disclosure Nos. 71439/1977, 73749/1979 and 72152/1980 and Japanese Pat. No. 374/1980.

However, the process for production of the intended compound (I) by using o-chlorophenylacetic acid in place of o-bromo- or o-iodophenylacetic acid has not been completed yet owing to the lower reactivity of the chlorine atom in substitution with aromatic amines.

On the other hand, E. D. Bergmann and Th. Billé-Samé [Bull. Soc. Chim. Fr., pp. 1090–1091 (1968)] reported that the reaction of o-chlorophenylacetic acid with aniline gave N-phenyloxyindole, biphenyl ether-2,2'-diacetic acid or the like.

This fact suggests that, in case o-chlorophenylacetic acid is used for production of the intended compound (I), the reaction may proceed in a different way from the reaction of o-bromo- or o-iodophenylacetic acid with 2,6-dichloroaniline disclosed in said Japanese Pat. No. 374/1980.

Thus, for production of the intended compound (I) from o-chlorophenylacetic acid and 2,6-dichloroaniline, it has been demanded to improve the selectivity of the reaction.

DETAILED DESCRIPTION OF THE INVENTION

As a result of intensive investigations made for the purpose of producing o-(2,6-dichloroanilino)phenylacetic acid (I) with a high yield by a simple step, the inventors have found that the intended compound (I) can be obtained by reacting o-chlorophenylacetic acid or an alkali metal salt thereof, in an ordinary reaction operation, with 2,6-dichloroaniline in the presence of a base and a specific quantitative range of copper catalyst such as a copper salt or copper powder in a polar solvent. The present invention has been completed on the basis of this finding.

The process of the present invention comprises, as shown below, reacting o-chlorophenylacetic acid (III) or an alkali metal salt thereof (IV) with 2,6-dichloroaniline (V) in the presence of a specific quantitative range of copper salt and/or copper powder and a base in a polar solvent.

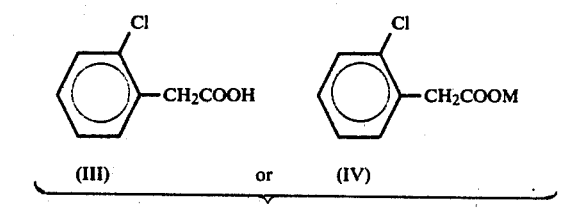

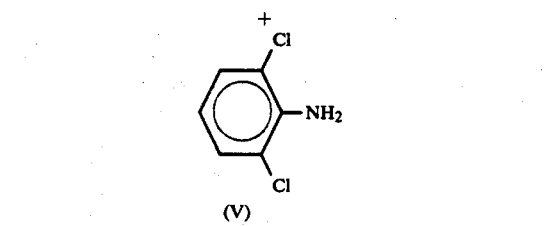

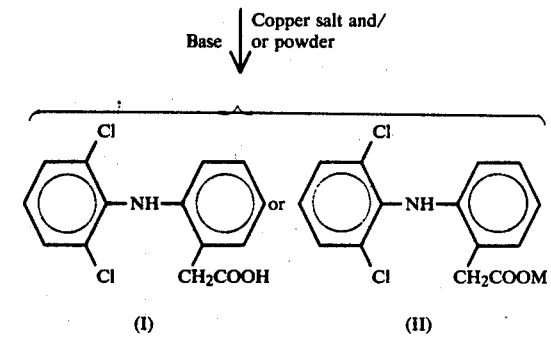

(wherein M represents an alkali metal atom.)

In the reaction of this process, at least 1 mol, preferably 3–5 mols, of 2,6-dichloroaniline (V), at least 0.5 mol, preferably 0.67–2 mols, of a copper salt and/or copper powder are used per mol of the starting compound (III) or (IV). The base is used in an amount of at least 2 gram equivalent per mol of the starting compound (III) or at least 1 gram equivalent per mol of the starting compound (IV).

As the starting compound, either free acid (III) or alkali metal salt thereof (IV) may be used.

As the copper salt, there may be used copper halides such as cuprous iodide and cuprous bromide. As the copper powder, there may be used commercially available copper powder or activated copper powder prepared specially. The activated copper powder may be prepared, for example, from cuprous iodide and metallic potassium or from copper sulfate and zinc. It is preferred in the process of the present invention to use cuprous iodide and/or activated copper powder.

As the base, potassium carbonate is used preferably.

As the solvent, there may be used an aprotic polar solvent such as N,N-dimethylformamide, 1,3-dimethyl-2-imidazolidinone or dimethyl sulfoxide. Among them, N,N-dimethylformamide is preferred.

The reaction is carried out preferably at 120°–160° C. with heating under an atmospheric pressure for 2–24 hours.

When a reaction accelerator such as an inorganic iodide, for example, potassium iodide, is further used in addition to the above copper salt and/or copper powder in the reaction, the reaction proceeds more rapidly.

o-(2,6-Dichloroanilino)phenylacetic acid (I) obtained by the above reaction is in the form of the free acid. If necessary, it may be converted to an alkali metal salt thereof (II) by an ordinary method after the isolation or during the work-up.

Thus, the process of the present invention is a quite excellent process for production of the intended compound (I), since the production process is simplified into one step and a high yield can be obtained. o-Chlorophenylacetic acid (III) used as the starting material in the present invention is far more easily available at a lower cost than other o-halogenophenylacetic acids, since it can be obtained from by-products formed in the production of agricultural chemicals. The process of the present invention is thus far more advantageous than the conventional processes.

The process of the present invention wherein o-chlorophenylacetic acid (III) or an alkali metal salt thereof (IV) is used as the starting material cannot be carried out in the same manner as in the conventional processes wherein o-bromophenylacetic acid or o-iodophenylacetic acid is used. This fact is apparent from the results of Comparative Example 1 which will be given below and wherein the intended compound (II) was obtained in only a trace amount by carrying out the process shown in Example 11 given in Japanese Pat. No. 374/1980 by which the highest yield could be obtained in the prior art.

As described above in detail, the process of the present invention is an excellent industrial process unlike the conventional processes.

The following examples and comparative examples further illustrate the present invention wherein pressure is an atmospheric pressure unless otherwise stated.

Production of o-(2,6-dichloroanilino)phenylacetic acid or sodium salt thereof

Example 1

A stirred mixture of 5.11 g of o-chlorophenylacetic acid, 24.30 g of 2,6-dichloroaniline, 8.28 g of potassium carbonate, 4.98 g of potassium iodide, 4.50 g of cuprous iodide and 60 ml of N,N-dimethylformamide was refluxed under a nitrogen atmosphere for 7 hours. The reaction mixture was filtered and the filtration residue was thoroughly washed with warm water. The washing solution was combined with the filtrate and n-butanol was added thereto. The mixture was concentrated under a reduced pressure. The concentration residue was thoroughly washed with chloroform and then diluted with icewater. It was then acidified with 2 N hydrochloric acid and extracted with chloroform. A 2 N aqueous sodium hydroxide solution was added to the chloroform layer and the whole was stirred at room temperature for 30 minutes and then cooled to precipitate crystals. Thus, 4.09 g (yield: 42.9%) of sodium o-(2,6-dichloroanilino)phenylacetate was obtained. 22% of unreacted o-chlorophenylacetic acid was recovered.

m.p. 283°–285° C. (decomp.)

Example 2

The same procedure as in Example 1 was employed except that cuprous iodide was replaced with 3.39 g of cuprous bromide to obtain 2.20 g (yield: 23.1%) of sodium o-(2,6-dichloroanilino)phenylacetate.

m.p. 283°–285° C. (decomp.)

Example 3

The same procedure as in Example 1 was employed except that cuprous iodide was replaced with 1.30 g of activated copper powder prepared from cuprous iodide and metallic potassium according to a method disclosed in "Journal of Organic Chemistry" Vol. 44, No. 19, p. 3445 (1979). 1.20 g of unreacted o-chlorophenylacetic acid was recovered and 2.87 g (yield: 30.1%) of sodium o-(2,6-dichloroanilino)phenylacetate was obtained.

m.p. 283°–285° C. (decomp.)

Example 4

The same procedure as in Example 1 was employed except that cuprous iodide was replaced with 1.30 g of activated copper powder prepared from copper sulfate and zinc to obtain 1.88 g (yield: 19.7%) of sodium o-(2,6-dichloroanilino)-phenylacetate.

m.p. 283°–285° C. (decomp.)

Comparative Example 1

The same procedure as in Example 11 given in Japanese Pat. No. 374/1980 was employed using 11.50 g of 2,6-dichloroaniline, 10.49 g of potassium carbonate, 2.00 g of potassium iodide, 0.75 g of activated copper powder (prepared from commercially available copper powder and iodine) and 28 ml of N-methyl-2-pyrrolidone except that potassium o-bromophenylacetate was replaced with 4.95 g of potassium o-chlorophenylacetate. A trace amount of sodium o-(2,6-dichloroanilino)-phenylacetate was obtained.

Comparative Example 2

The same procedure as in Example 1 given in Japanese Pat. No. 374/1980 was employed using 3.10 g of 2,6-dichloroaniline, 0.10 g of cuprous bromide, 2.80 g of potassium carbonate and 10 ml of dimethyl sulfoxide except that potassium o-bromophenylacetate was replaced with 4.17 g of potassium o-chlorophenylacetate. o-(2,6-Dichloroanilino)phenylacetic acid was not obtained at all.

What is claimed is:

1. A process for production of o-(2,6-dichloroanilino)-phenylacetic acid which comprises reacting an o-chlorophenylacetic acid compound selected from the group consisting of o-chlorophenylacetic acid and alkali metal salts thereof with 2,6-dichloroaniline in the presence of a base and at least 0.5 mol of a copper catalyst per mol of o-chlorophenylacetic acid, said copper catalyst being selected from the group consisting of a copper salt, a copper powder and a mixture thereof.

2. A process as set forth in claim 1 wherein said copper salt is a cuprous halide and said copper powder is activated one which is prepared from copper sulfate and zinc.

3. A process as set forth in claim 1 wherein said copper salt is a cuprous halide and said copper powder is activated one which is prepared from cuprous iodide and metallic potassium.

4. A process as set forth in claim 1 wherein the reaction system contains a reaction accelerator comprising an inorganic iodide.

5. A process as set forth in claim 4 wherein the reaction accelerator is potassium iodide.

6. A process as set forth in claim 1 wherein at least one mole of the 2,6-dichloroaniline is present per mole of the o-chlorophenylacetic acid compound.

7. A process as set forth in claim 1 wherein from 3 to 5 moles of the 2,6-dichloroaniline is present per mole of the o-chlorophenylacetic acid compound.

8. A process as set forth in claims 1, 2, 3, 4, 5, 6 or 7 wherein from 0.67 to 2 moles of the copper catalyst is present.

9. A process as set forth in claim 1, 2, 3, 4, 5, 6 or 7 wherein the base is present in an amount of at least 2 gram equivalent per mole of o-chlorophenylacetic acid or at least 1 gram equivalent per mole of an alkaline metal salt of o-chlorophenylacetic acid.

10. A process as set forth in claim 9 wherein the base is potassium carbonate.

11. A process as set forth in claim 1, 2, 3, 4, 5, 6 or 7 which takes place in an aprotic polar solvent.

12. A process as set forth in claim 11 wherein the aprotic polar solvent is N,N-dimethylformamide, 1,3-dimethyl-2-imidazolidinone or dimethyl sulfoxide.

* * * * *